(12) United States Patent
Kawanishi

(10) Patent No.: US 10,891,733 B2
(45) Date of Patent: Jan. 12, 2021

(54) RADIOGRAPHING SYSTEM, RADIOGRAPHING METHOD, CONTROL APPARATUS, AND STORAGE MEDIUM

(71) Applicant: CANON KABUSHIKI KAISHA, Tokyo (JP)

(72) Inventor: Tomohiro Kawanishi, Tachikawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 239 days.

(21) Appl. No.: 16/190,804

(22) Filed: Nov. 14, 2018

(65) Prior Publication Data

US 2019/0156480 A1 May 23, 2019

(30) Foreign Application Priority Data

Nov. 22, 2017 (JP) ................. 2017-224974

(51) Int. Cl.
| | | |
|---|---|---|
| *G06T 7/00* | (2017.01) | |
| *G06T 11/60* | (2006.01) | |
| *G06F 3/0481* | (2013.01) | |
| *G16H 30/40* | (2018.01) | |
| *G01N 23/04* | (2018.01) | |

(Continued)

(52) U.S. Cl.
CPC .......... G06T 7/0014 (2013.01); A61B 6/5211 (2013.01); G01N 23/04 (2013.01); G06F 3/04817 (2013.01); G06T 7/0012 (2013.01); G06T 11/001 (2013.01); G06T 11/60 (2013.01); G16H 30/40 (2018.01); *G06T 2207/10116* (2013.01); *G06T 2207/30061* (2013.01); *G06T 2210/41* (2013.01)

(58) Field of Classification Search
CPC ................. G06T 7/0012; G06T 7/0014; G06T 2207/10116; G06T 2207/30061; A61B 6/5211; G01N 23/04
See application file for complete search history.

(56) References Cited

U.S. PATENT DOCUMENTS

| | | | | |
|---|---|---|---|---|
| 10,015,308 B2 * | 7/2018 | Cho | .................... | H04N 5/23293 |
| 2005/0243347 A1 * | 11/2005 | Hayaishi | ............... | G06T 11/001 |
| | | | | 358/1.9 |

(Continued)

FOREIGN PATENT DOCUMENTS

JP   2013-208396 A   10/2013

*Primary Examiner* — Michael C Bryant
(74) *Attorney, Agent, or Firm* — Canon U.S.A., Inc. IP Division

(57) ABSTRACT

Provided is a radiographing system that can efficiently generate a plurality of radiographic images having undergone plural types of image processing and can separately store the plurality of radiographic images. The radiographing system includes an image acquisition unit that acquires a radiographic image based on radiation transmitted through a subject, an image processing setting unit that sets plural types of image processing to a specific imaging procedure, an image processing unit that executes the plural types of image processing set by the image processing setting unit on a radiographic image acquired by the specific imaging procedure to generate a plurality of radiographic images, and an output unit that outputs, to a storage device, the plurality of radiographic images generated by the image processing unit separately according to a type of the image processing.

18 Claims, 10 Drawing Sheets

(51) Int. Cl.
*G06T 11/00* (2006.01)
*A61B 6/00* (2006.01)

(56) References Cited

U.S. PATENT DOCUMENTS

2014/0176612 A1* 6/2014 Tamura ..................... G06T 3/40
 345/660
2016/0300351 A1* 10/2016 Gazit ...................... G06T 7/187

* cited by examiner

FIG. 8A
IMAGE OUTPUT SETTING — 800

NAME: CHEST FRONT PNEUMOCONIOSIS — 802

OUTPUT SETTING:
☑ SET AS SPECIFIC PROCESSING 1 — 804

CANCEL — 808
OK — 806

FIG. 8B
IMAGE STORAGE SETTING — 810

STORAGE NAME: ▶ STORAGE DEVICE C — 812
STORAGE DEVICE A
STORAGE DEVICE B
STORAGE DEVICE C

OUTPUT CONDITION: ☑ SPECIFIC PROCESSING 1 — 814

CANCEL — 818
OK — 816

IMAGE OUTPUT SETTING — 800

NAME: [CHEST FRONT BLACK/WHITE INVERSION] — 802

OUTPUT SETTING:
☑ SET AS SPECIFIC PROCESSING 2 — 804

[CANCEL] — 808    [OK] — 806

FIG.9B

IMAGE STORAGE SETTING — 810

STORAGE NAME:
▶ STORAGE DEVICE B — 812
  STORAGE DEVICE A
  STORAGE DEVICE B
  STORAGE DEVICE C

OUTPUT CONDITION: ☑ SPECIFIC PROCESSING 2 — 814

[CANCEL] — 818    [OK] — 816

124

RADIOGRAPHING SYSTEM, RADIOGRAPHING METHOD, CONTROL APPARATUS, AND STORAGE MEDIUM

BACKGROUND

Field

The present disclosure relates to a radiographing system, a radiographing method, a control apparatus, and a storage medium storing a program and, in particular, relates to a technique for applying plural types of image processing to a radiographic image.

Description of the Related Art

In recent years, hospitals have been installing a hospital information system using a network. For example, if a doctor determines that a subject needs to undergo radiographing, an examination instruction is input from a hospital information system (HIS) terminal to transmit an examination order to a radiography department that is a request destination.

A radiographing system executes radiographing based on the examination order. A captured radiographic image is transferred to a picture archiving and communication system (PACS) and/or is printed. There can be cases in which plural types of image processing are executed on the captured radiographic image. For example, in the case of a pneumoconiosis examination, predetermined image processing for pneumoconiosis is applied to the radiographic image in addition to normal image processing (see Japanese Patent Application Laid-Open No. 2013-208396). The technique discussed in Japanese Patent Application Laid-Open No. 2013-208396, however, requires an operation to duplicate a captured radiographic image and an operation to adjust an image processing parameter in order to generate a radiographic image having undergone the plural types of image processing.

SUMMARY

The present disclosure is directed to a radiographing system that efficiently generates a plurality of radiographic images having undergone plural types of image processing.

According to an aspect of the present disclosure, a radiographing system includes an image acquisition unit that acquires a radiographic image based on radiation transmitted through a subject, an image processing setting unit that sets plural types of image processing to a specific imaging procedure, an image processing unit that executes the plural types of image processing set by the image processing setting unit on a radiographic image acquired by the specific imaging procedure to generate a plurality of radiographic images, and an output unit that outputs, to a storage device, the plurality of radiographic images generated by the image processing unit separately according to a type of the image processing.

Further features will become apparent from the following description of exemplary embodiments with reference to the attached drawings.

BRIEF DESCRIPTION OF THE DRAWINGS

FIGS. 8A and 8B illustrate an setting screen of an output setting unit of the radiographing system according to an exemplary embodiment.

FIGS. 9A and 9B illustrate an example of the setting screen of the output setting unit of the radiographing system according to an exemplary embodiment.

DESCRIPTION OF THE EMBODIMENTS

An exemplary embodiment will be described below with reference to the attached drawings.

Figure 1:
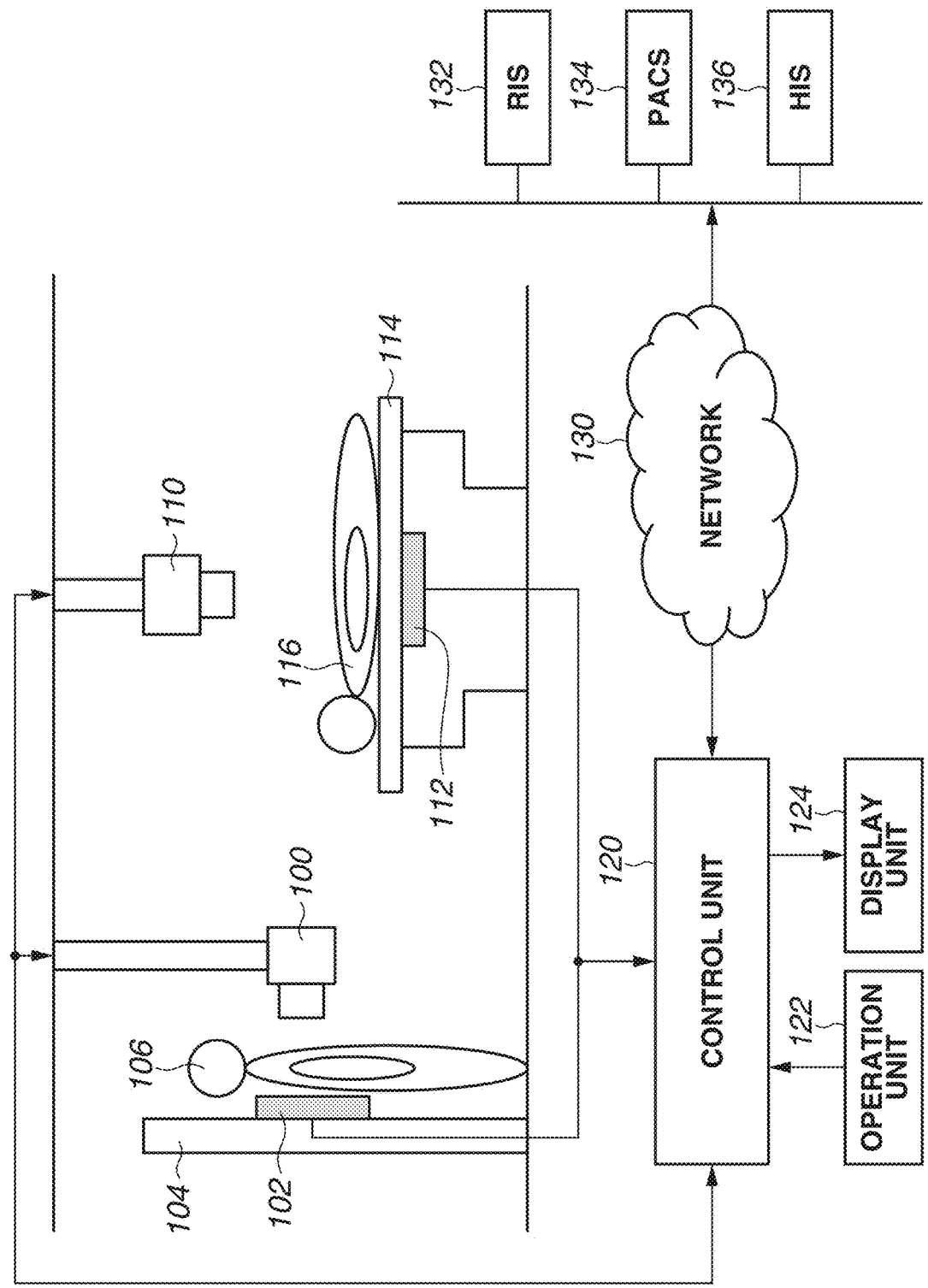
FIG. 1 illustrates an entire configuration of a radiographing system according to an exemplary embodiment.

A radiographing system according to an exemplary embodiment is described with reference to FIG. 1. As illustrated in FIG. 1, two sets of a radiation generation unit and an imaging table are disposed in an imaging room. In the imaging room, a radiation generation unit 100, a radiation detection apparatus 102, and an imaging stand 104 are disposed. The radiation generation unit 100 emits radiation. The radiation detection apparatus 102 detects the radiation transmitted through a subject 106. The imaging stand 104 supports the radiation detection apparatus 102. The imaging stand 104 is a standing position imaging table. Similarly, there are disposed a radiation generation unit 110 that emits radiation, a radiation detection apparatus 112 that detects the radiation transmitted through a subject 116, and an imaging table 114 that supports the radiation detection apparatus 112. The imaging table 114 is a lying position imaging table.

The radiographing system includes a display unit 124, an operation unit 122, and a control unit (control apparatus) 120. The display unit 124 is connected to the control unit 120 and displays a radiographic image and various types of information. The operation unit 122 is operated by an operator. The control unit 120 sets imaging conditions (e.g., tube voltage, tube current, and irradiation time) to the radiation generation units 100 and 110, executes image processing on radiographic images output from the radiation detection apparatuses 102 and 112, and executes various types of control thereon. The control unit 120 functions as a display control unit of the display unit 124.

The control unit 120 is connected with a radiology information system (RIS) 132, a picture archiving and communication system (PACS) 134, and a hospital information system (HIS) 136 via a network 130. The RIS 132 transmits an examination order to the control unit 120. The PACS 134 manages the radiographic images. The HIS 136 manages progress of an examination.

If a radiography department of a hospital receives an examination order via the RIS 132, the radiography department adds imaging information (e.g., imaging condition and imaging procedure) about radiographing to the examination order and transmits the resulting examination order to the control unit 120. The control unit 120 executes radiographing based on the received examination order. Then, the control unit 120 adds attendant information including the examination order to a captured radiographic image and outputs the resulting radiographic image.

The PACS 134 is a server mainly used for image management. The PACS 134 includes a storage device that stores the radiographic images and the attendant information. On a high-definition monitor connected to the PACS 134, a radiographic image checking operation, detailed post processing, diagnosis operation, etc. are executed. As described above, the radiographic image output from the control unit 120 is transmitted to the PACS 134.

The HIS 136 is a hospital management system and includes a server that manages accounting information. In a case of executing radiographing, the operator inputs an examination instruction to a terminal of the HIS 136. Then, the examination instruction is transmitted from the HIS 136 to a request destination, which is the radiography department of the hospital. Such request information is referred to as the examination order. The examination order includes the department name of a request source, an examination item, personal data of the subject, etc. Execution information about the examination by the radiographing system is transmitted to the HIS 136. The execution information transmitted to the HIS 136 is used not only for progress management of the examination but also for accounting processing after the examination.

The control unit 120, the RIS 132, the PACS 134, and the HIS 136 are connected via the network 130 including, for example, a local area network (LAN) or a wide area network (WAN).

The apparatuses described above includes one or more computers. Each of the computers includes a main control unit such as a central processing unit (CPU) and a storage device such as a read-only memory (ROM) and a random access memory (RAM). The computer can also include a communication unit such as a network card, an input/output unit such as a keyboard, a display, and a touch panel, and the like. These components are connected via a bus and the like, and the main control unit executes a program stored in the storage device to control the components.

The control unit 120 is connected with the radiation generation units 100 and 110. More specifically, the control unit 120 is connected with the radiation generation units 100 and 110 via a wired or wireless network or a dedicated line. The control unit 120 sets radiographing conditions of the radiation generation units 100 and 110 and controls generation of radiation by the radiation generation units 100 and 110. The radiation generation units 100 and 110 function as radiation sources that generate the radiation. The radiation generation units 100 and 110 are achieved by, for example, X-ray tubes and irradiate the subjects 106 and 116 (e.g., specific areas of the subjects), respectively, with the radiation.

Each of the radiation generation units 100 and 110 can irradiate a desired irradiation range with the radiation. Each of the radiation generation units 100 and 110 is installed via a support portion provided to a floor or a ceiling. On an irradiation surface of each of the radiation generation units 100 and 110, there is provided a diaphragm (not illustrated) that blocks the radiation. The operator can set the irradiation range of the radiation emitted from each of the radiation generation units 100 and 110 by controlling the diaphragm that blocks the radiation.

The radiographing system includes the radiation detection apparatuses 102 and 112 that detect the radiation emitted from the radiation generation units 100 and 110, respectively. The radiation detection apparatuses 102 and 112 detect the radiation transmitted through the subjects 106 and 116, respectively, and output image data corresponding to the radiation. The image data can also be referred to as a radiographic image.

More specifically, each of the radiation detection apparatuses 102 and 112 detects the radiation transmitted through the subject 106 or 116 as a charge corresponding to an amount of the transmitted radiation. For example, each of the radiation detection apparatuses 102 and 112 uses a direct conversion sensor that directly converts radiation into a charge such as amorphous selenium (a-Se), or an indirect sensor using a scintillator such as cesium iodide (CsI) and a photoelectric conversion element such as amorphous silicon (a-Si). Further, the radiation detection apparatuses 102 and 112 perform an analog/digital (A/D) conversion on the detected charge to generate a radiographic image, and output the generated radiographic image to the control unit 120.

The operation unit 122 is used for operating the radiographing system. The operation unit 122 includes, for example, a mouse and operation icons, and inputs various instructions from the operator to a component device. The display unit 124 is achieved by, for example, a liquid crystal display, and displays various types of information to the operator (e.g., radiographer, doctor). The display unit 124 and the operation unit 122 can be integrated and achieved as a touch panel.

The control unit 120 is connected with the radiation detection apparatuses 102 and 112. More specifically, the control unit 120 is connected with the radiation detection apparatuses 102 and 112 via a wired or wireless network or a dedicated line. The radiation detection apparatuses 102 and 112 image the radiation emitted from the radiation generation units 100 and 110, respectively, and output radiographic images to the control unit 120. The control unit 120 includes an application function that rims on the computer. The control unit 120 controls the operations of the radiation detection apparatuses 102 and 112, and outputs the radiographic image and a graphical user interface (GUI) to the display unit 124. The control unit 120 includes a function of executing image processing such as noise removal, gradation processing, and enhancement processing on the radiographic image output from the radiation detection apparatuses 102 or 112. The control unit 120 can also perform image processing such as trimming and rotation on the radiographic image output from the radiation detection apparatuses 102 or 112. The display unit 124 displays the radiographic image output from the control unit 120.

Figure 2:
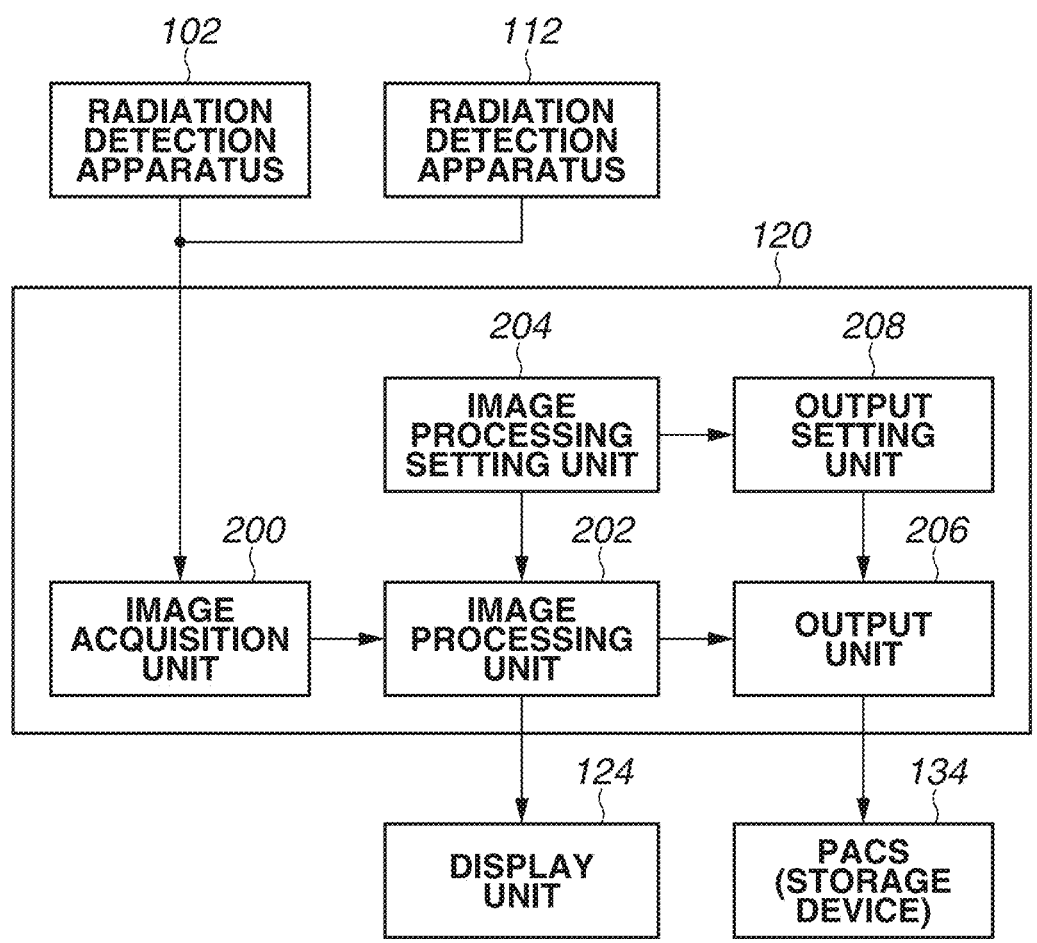
FIG. 2 illustrates a configuration of a control unit of the radiographing system according to an exemplary embodiment.

Details of the control unit 120 are described with reference to FIG. 2. As illustrated in FIG. 2, the control unit 120 includes an image acquisition unit 200, an image processing unit 202, an image processing setting unit 204, an output unit 206, and an output setting unit 208. The image acquisition unit 200 acquires the radiographic image (image data) output from the radiation detection apparatuses 102 and 112. The image processing unit 202 executes image processing on the radiographic image acquired by the image acquisition unit 200. The image processing setting unit 204 sets image processing to be executed by the image processing unit 202. The output unit 206 outputs the radiographic image having undergone the image processing executed by the image processing setting unit 204 to an external apparatus (PACS (storage device)). The output setting unit 208 sets an output from the output unit 206. In the control unit 120, the computer executes a program stored in a memory (RUM, RAM) to execute various types of processing.

The control unit 120 displays the radiographic image output from the image processing unit 202 on the display unit 124. The display unit 124 displays the radiographic image that has undergone the image processing executed by the image processing unit 202 and is output from the image processing unit 202. The display unit 124 can also display setting information about the image processing executed by the image processing setting unit 204 and setting information about the output executed by the output setting unit 208. Thus, the operator can understand the type of image processing executed by the image processing unit 202 and an output destination of the radiographic image from the output unit 206. Then, the operator can operate, via the operation unit 122, the setting information about the image processing executed by the image processing setting unit 204 and the setting information about the output executed by the output setting unit 208.

The PACS (storage device) 134 stores the radiographic image output from the output unit 206. The PACS 134 stores the radiographic images having undergone a plurality of types of image processing executed by the image processing unit 202 separately according to the type of image processing. The PACS 134 stores the radiographic images together with image processing information, subject information, etc.

The image processing unit 202 can execute plural types of image processing on the radiographic image based on the image processing information set by the image processing setting unit 204. In other words, the image processing unit 202 can add a type of image processing to be performed on one radiographic image. For example, the image processing unit 202 executes normal image processing, black/white inversion processing, and processing for pneumoconiosis on one radiographic image to generate a plurality of radiographic images. The normal image processing is the processing of executing gradation conversion, etc. on the radiographic image output from the image acquisition unit 200 to convert a pixel value into a density (luminance). The black/white inversion processing is the processing of inverting the black and white of the density (luminance) in the radiographic image generated by the normal image processing. The black/white inversion processing is effective processing for enhancing white and gray parts in a region displayed in black in the radiographic image generated by the normal image processing. The processing for pneumoconiosis is the processing of generating a radiographic image by applying predetermined image processing for pneumoconiosis in addition to the radiographic image generated by applying the normal image processing. More specifically, the processing for pneumoconiosis is different from the normal image processing in terms of image processing parameters relating to gradation conversion for each frequency component, luminance, contrast, edge enhancement, and noise removal.

The normal image processing can be referred to as first image processing, and the image processing such as the black/white inversion processing and the processing for pneumoconiosis can be referred to as second image processing. More specifically, the image processing unit 202 can execute the first image processing (normal image processing) and the second image processing (added image processing) on one radiographic image to generate the plurality of radiographic images.

In the present exemplary embodiment, the image processing unit 202 applies the black/white inversion processing and the processing for pneumoconiosis to generate the plurality of radiographic images while retaining the radiographic image having undergone the normal image processing. More specifically, the image processing unit 202 generates the radiographic image having undergone the normal image processing and the radiographic image having undergone at least one of the black/white inversion processing and the processing for pneumoconiosis.

The image processing unit 202 stores one or more image processing parameters for each imaging procedure. For example, one or more image processing parameters are stored for each imaging such as imaging at a chest front, imaging at a chest side, imaging at an abdomen front, and imaging at an abdomen side. In the imaging at the chest front, three types of image processing parameters relating to the normal image processing, the black/white inversion processing, and the processing for pneumoconiosis are stored. In the imaging at the abdomen front, the processing for pneumoconiosis is unnecessary, whereby two types of image processing parameters relating to the normal image processing and the black/white inversion processing are stored. The operator can set imaging processing for each imaging procedure via the image processing setting unit 204.

Figure 3:
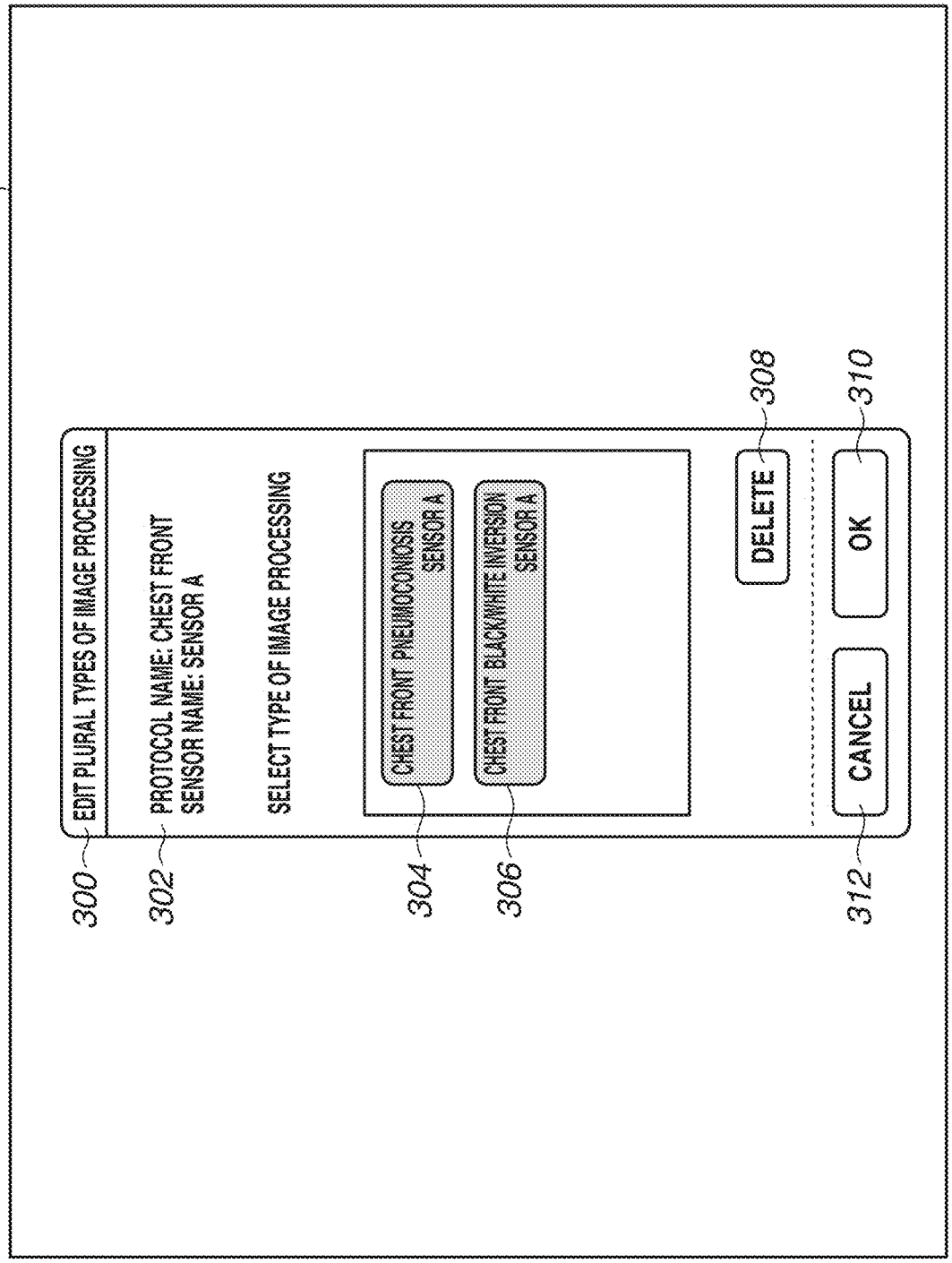
FIG. 3 illustrates an example of a setting screen of an image processing setting unit of the radiographing system according to an exemplary embodiment.

FIG. 3 illustrates a setting screen of the image processing setting unit 204 displayed on the display unit 124. The setting screen of the image processing setting unit 204 is displayed on the display unit 124. Various icons and tags are selected using the operation unit 122 to be executed.

As illustrated in FIG. 3, on a menu 300 for editing plural types of image processing, there are displayed an imaging procedure (protocol name, sensor name) 302, image processing icons 304 and 306 for selecting image processing settable in the imaging procedure, a delete icon 308 for deleting the selected image processing icon, an OK icon 310 for determining contents of the editing of the plural types of image processing in the imaging procedure, and a cancel icon 312 for canceling the editing of the plural types of image processing in the imaging procedure.

On the menu 300 for editing the image processing, the image processing icons 304 and 306 relating to the image processing to be added are displayed. The image processing icon of the normal image processing is not displayed thereon because the normal image processing is executed on every radiographic image, whereby the normal image processing does not have to be selected.

In the present exemplary embodiment, "PROTOCOL NAME: CHEST FRONT" and "SENSOR NAME: SENSOR A" are displayed as the imaging procedure (protocol name, sensor name) 302. The operator can change the imaging procedure (protocol name and sensor name) as desired via the operation unit 122. Then, the image processing setting unit 204 can set the type of image processing for each of the imaging procedures. The image processing information set by the image processing setting unit 204 is transmitted to the image processing unit 202.

In the imaging procedure illustrated in FIG. 3, the icon 304 for executing the processing for pneumoconiosis and the icon 306 for executing the black/white inversion processing are displayed. By pressing the icon 304 for executing the processing for pneumoconiosis, the operator can cause the image processing unit 202 to generate a radiographic image by applying the predetermined image processing for pneumoconiosis in addition to the radiographic image generated by applying the normal image processing. If the icon 304 for executing the processing for pneumoconiosis is pressed, the display form (e.g., color, frame, etc. of the icon 304) of the icon 304 changes. The operator can recognize that the icon 304 for executing the processing for pneumoconiosis has been pressed.

By pressing the icon 306 for executing the black/white inversion processing, the operator can cause the image processing unit 202 to generate a radiographic image by applying the processing of inverting the black and white of the density (luminance n the radiographic image generated by the normal image processing. If the icon 306 for executing the black/white inversion processing is pressed, the display form (e.g., color, frame, etc. of the icon 306) of the icon 306 changes. The operator can recognize that the icon 306 for executing the black/white inversion processing has been pressed. For example, in FIG. 3, the display forms of the icon 304 for executing the processing for pneumoconiosis and the icon 306 for executing the black/white inversion processing are changed in color. The operator can recognize that the image processing corresponding to each of the icons 304 and 306 has been selected.

While the processing for pneumoconiosis and the black/white inversion processing are described as selectable in the imaging at the chest front in the present exemplary embodiment, the selectable processing is not limited to those described above, and various processing can be selected such as noise reduction processing, edge enhancement processing, vertical inversion processing, horizontal inversion processing, enlargement processing, and reduction processing.

Figure 4:
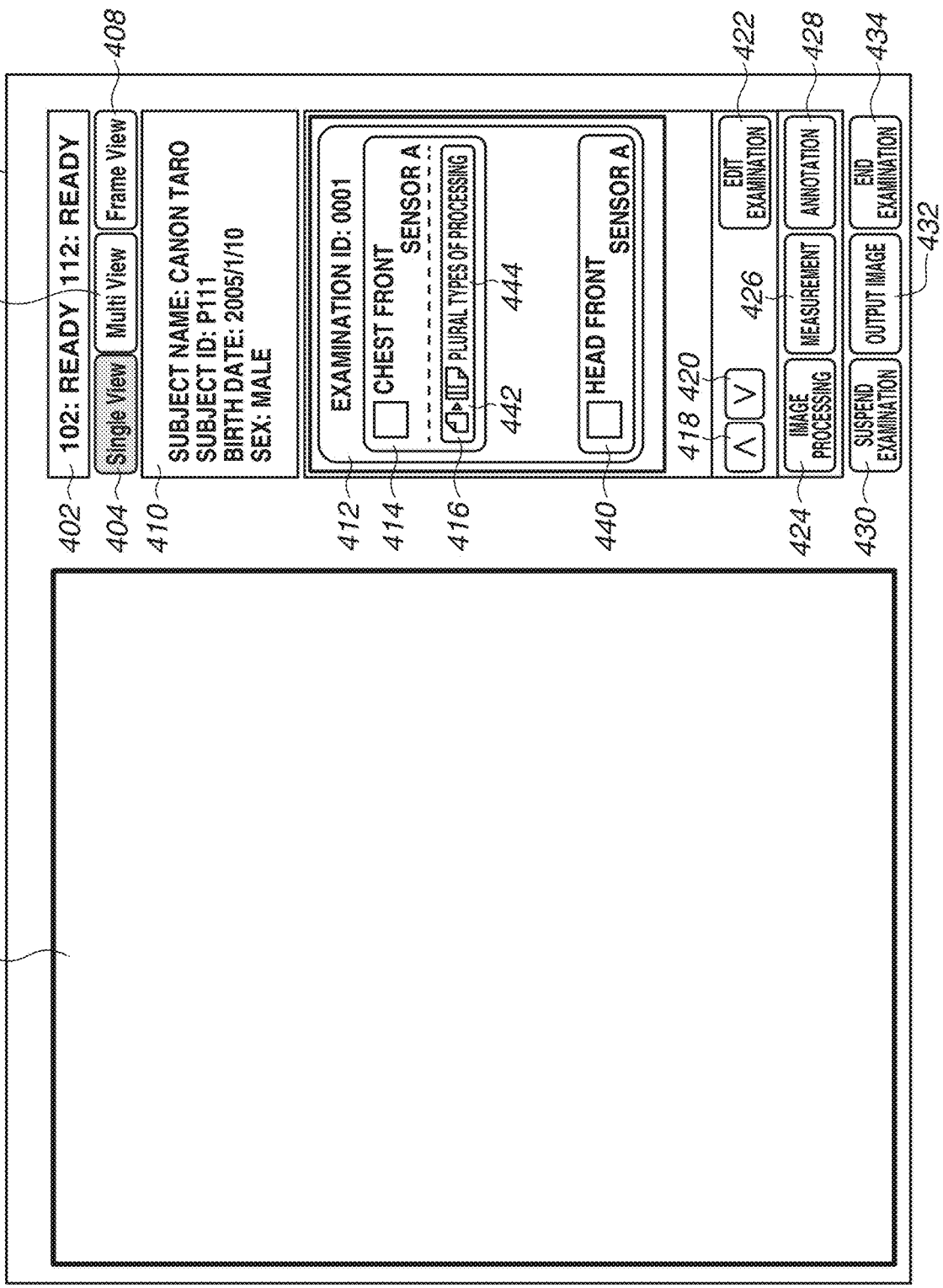
FIG. 4 illustrates an example of a display screen displayed before the radiographing system according to an exemplary embodiment executes imaging.

FIG. 4 illustrates a display screen of the display unit 124 displayed before imaging. The control unit 120 can control the display screen of the display unit 124. The display screen of the display unit 124 includes an image display region 400 for displaying a radiographic image. The display screen of the display unit 124 also includes a status display region 402 for displaying statuses of the radiation detection apparatuses 102 and 112, a single-view icon 404, a multi-view icon 406, and a frame-view icon 408.

The display screen of the display unit 124 includes a subject display region 410 for displaying subject information, and an examination information display region 412 for displaying examination information. The examination information display region 412 includes imaging procedure icons 414 and 440 for displaying an imaging procedure to be executed, and a display region 416 relating to plural types of image processing to display that plural types of image processing are available for the imaging procedure. The imaging procedure icons 414 and 440 can also be referred to as an imaging protocol.

The display screen of the display unit 124 includes an order move-up icon 418, an order move-down icon 420, an edit examination icon 422, an image processing icon 424, a measurement icon 426, an annotation edit icon 428, a suspend examination icon 430, an output image icon 432, and an end examination icon 434.

The image display region 400 displays a captured radiographic image. In a case where a display target is switched after the imaging, a selected radiographic image is displayed. As needed, the image display region 400 can display the subject information, the examination information, the imaging condition, etc.

The status display region 402 is a region for displaying the statuses of the radiation detection apparatuses 102 and 112 in different colors and characters so that the operator can easily distinguish the statuses. Since the radiographing system includes the two radiation detection apparatuses 102 and 112 as illustrated in FIG. 1, the status display region 402 can be displayed to display each of the statuses of the radiation detection apparatuses 102 and 112.

The control unit 120 having received the statuses from the radiation detection apparatuses 102 and 112 transmits the statuses to the display unit 124. For example, in a case where the radiation detection apparatuses 102 and 112 are undetectable, the status display region 402 displays "NOT READY". In a case where the radiation detection apparatuses 102 and 112 are detectable, the status display region 402 displays "READY". A background color of "READY" is changed to a color distinguishable from a background color of "NOT READY".

The single-view icon 404 is an icon for switching to a single view in which a single flame of the selected radiographic image is displayed in the image display region 400. In a case of an image having a plurality of frames, another frame can be displayed or a moving image can be reproduced by operating the operation unit 122 while a preview is displayed. The multi-view icon 406 is an icon for switching to a multi view in which the image display region 400 is divided into multiple lattice-shaped display regions and images captured during an examination being executed are parallel-displayed. The frame-view icon 408 is an icon for switching to a frame view in which the image display region 400 is divided into multiple lattice-shaped display regions and frame images of a moving image are parallel-displayed.

The subject display region 410 is a region for displaying the subject information such as the subject name, subject identifier (ID), birth date, and sex. The examination information display region 412 displays an examination ID relating to the imaging, and the imaging procedure icons 414 and 440 including the imaging procedure. The imaging procedure icons 414 and 440 display the imaging procedure including a name of the imaging procedure and a name of the radiation detection apparatus, and a thumbnail of a radiographic image if imaging is executed. If imaging is not executed yet, a thumbnail indicating an imaging orientation is displayed. The thumbnail indicating the imaging orientation includes information about the imaging tables 104 and 114 supporting the radiation detection apparatuses 102 and 112, respectively. Thus, the operator can recognize whether imaging by the imaging procedure has been executed by checking the displayed contents of the thumbnail.

In the present exemplary embodiment, in the imaging procedure relating to the imaging procedure icon 414, plural types of image processing are to be executed on the radiographic image imaged by the imaging procedure relating to the imaging procedure icon 414 (chest front). In the imaging procedure relating to the imaging procedure icon 440, plural types of image processing are not to be executed and only the normal image processing is to be executed on the radiographic image imaged by the imaging procedure relating to the imaging procedure icon 440 (head front). More specifically, the imaging procedure icons 414 and 440 are displayed so that the case in which plural types of image processing are to be executed and the case in which plural types of image processing are not to be executed are distinguishable.

In the imaging procedure icon 414 for executing plural types of image processing, the display region 416 relating to plural types of image processing is displayed. In the display region 416 relating to plural types of image processing, a plural types of image processing icon 442 indicating that plural types of image processing are to be executed, and text information 444 indicating that the plural types of image processing are be executed are displayed. The text information 444 is displayed as, for example, "PLURAL TYPES OF IMAGE PROCESSING". In the plural types of image processing icon 442, a left image indicates that a single radiographic image is generated, and a right image indicates that a plurality of radiographic images (e.g., three images) is generated. More specifically, the plural types of image processing icon 442 indicates that the plural types of image processing are to be executed on one radiographic image to generate a plurality of radiographic images. Since the display region 416 relating to plural types of image processing is displayed within the imaging procedure icon 414 for executing the plural types of image processing, a display size of the imaging procedure icon 414 is greater than a display size of the imaging procedure icon 440 for not executing the plural types of image processing. A display form such as color and shape of the imaging procedure icon 414 for executing plural types of image processing can be changed to any form as long as the operator can recognize whether the imaging procedure icon 414 is an imaging procedure icon for executing the plural types of image processing.

As described above, the control unit 120 causes the display unit 124 to display information about the plural types of image processing in the imaging procedure icon 414 corresponding to a specific imaging procedure. Thus, the display unit 124 can display the information about the plural types of image processing in the imaging procedure icon 414 corresponding to a specific imaging procedure (chest front).

The control unit 120 causes the display unit 124 to display either the plural types of image processing icon 442 indicating that the plural types of image processing are to be executed or the text information 444 indicating that the plural types of image processing are to be executed. The display unit 124 can display either the plural types of image processing icon 442 indicating that the plural types of image processing are to be executed or the text information 444 indicating that the plural types of image processing are to be executed.

In the case where the image processing setting unit 204 sets image processing such as the black/white inversion processing and the processing for pneumoconiosis in addition to the normal image processing, the display region 416 relating to plural types of image processing displays information indicating that the plural types of image processing are set. More specifically, if the image processing setting unit 204 sets the plural types of image processing to the chest front imaging procedure, the control unit 120 transmits, to the display unit 124, a notification that the plural types of image processing are set to the chest front imaging procedure. The display unit 124 displays the display region 416 relating to plural types of image processing in the imaging procedure icon 414 of the chest front imaging procedure.

The operator can recognize that the plural types of image processing are set to the imaging procedure displayed in the imaging procedure icon 414 by checking the display region 416 relating to plural types of image processing. In the present exemplary embodiment, the operator can recognize that the plural types of image processing are set to the chest front imaging procedure. The operator can also recognize that only the normal image processing is set to a head front imaging procedure.

The order move-up icon 418 is an icon for providing an instruction to move up the order of execution of the imaging procedure. The order move-down icon 420 is an icon for providing an instruction to move down the order of execution of the imaging procedure. The edit examination icon 422 is an icon for providing an instruction to change to, for example, the setting screen of the image processing setting unit 204 illustrated in FIG. 3. The image processing icon 424 is an icon for providing a switch instruction to display or not to display the image processing. The measurement icon 426 is an icon for providing a switch instruction to display or not to display a measurement operation function. The annotation edit icon 428 is an icon for providing a switch instruction to display or not to display an annotation. The suspend examination icon 430 is an icon for providing an instruction to suspend an examination being executed. The output image icon 432 is an icon for providing an instruction to output the radiographic image included in the examination being executed. The end examination icon 434 is an icon for receiving an input operation to end the examination including at least one imaging.

Figure 5:
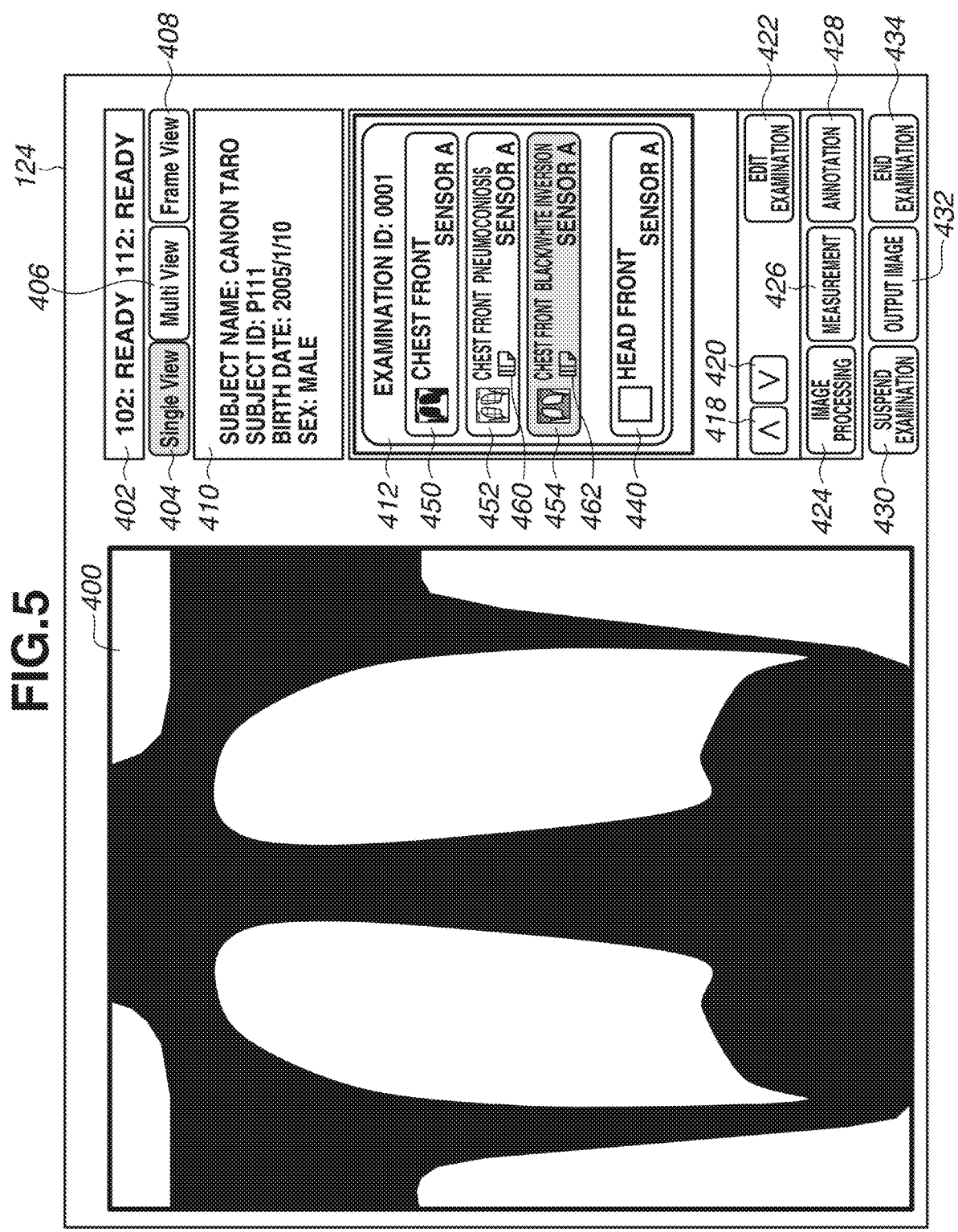
FIG. 5 illustrates an example of a display screen displayed after the radiographing system according to an exemplary embodiment executes imaging.

FIG. 5 illustrates the display screen of the display unit 124 after the imaging by the specific imaging procedure to which the plural types of image processing are set. The difference between the display screen of the display unit 124 in FIG. 5 and the display screen thereof in FIG. 4 is the image display region 400 and the examination information display region 412.

In FIG. 4, the plural types of image processing are set to the chest front imaging procedure, and the display region 416 relating to plural types of image processing is displayed.

If the chest front imaging procedure to which the plural types of image processing are set s executed, the display form is changed to a display form as illustrated in FIG. 5. In the image display region 400, the imaged radiographic image is displayed. The imaging procedure icon 414 indicating the chest front imaging procedure illustrated in FIG. 4 is divided (duplicated) into imaging procedure icons 450, 452, and 454 for each image processing and is displayed. In the present exemplary embodiment, the processing for pneumoconiosis and the black/white inversion processing are set by the image processing setting unit 204, whereby the three imaging procedure icons 450, 452, and 454 of the normal image processing, the processing for pneumoconiosis, and the black/white inversion processing, respectively, are displayed.

The imaging procedure icon 450 is an icon corresponding to the normal image processing. In the imaging procedure icon 450, a thumbnail of the radiographic image having undergone the normal image processing is displayed. The imaging procedure icon 454 is an icon corresponding to the black/white inversion processing. In the imaging procedure icon 454, a duplication mark 462 indicating that image processing different from the normal image processing is applied to make a duplicate is displayed. In the imaging procedure icon 454, a thumbnail of the radiographic image having undergone the black/white inversion processing is displayed. The imaging procedure icon 452 is an icon corresponding to the processing for pneumoconiosis. In the imaging procedure icon 452, a duplication mark 460 indicating that image processing different from the normal image processing is applied to make a duplicate is displayed. In the imaging procedure icon 452, a thumbnail of the radiographic image having undergone the processing for pneumoconiosis is displayed.

As described above, the duplication marks 460 and 462 indicating that the plural types of image processing are applied to duplicate the radiographic image are displayed in the imaging procedure icons 452 and 454, respectively.

After the imaging by the specific imaging procedure to which the plural types of image processing are set, the radiographic image corresponding to the imaging procedure icon 454, which is located at the lowermost position among the imaging procedure icons 450, 452, and 454, is displayed in the image display region 400. Since the imaging procedure icon 454 is the icon corresponding to the black/white inversion processing, the radiographic image having undergone the black/white inversion processing is displayed in the image display region 400. A display form such as color and shape of the imaging procedure icon 454 corresponding to the radiographic image displayed in the image display region 400 is changed. Since the imaging procedure icon 454 is the icon corresponding to the black/white inversion processing, the operator can recognize that the radiographic image having undergone the black/white inversion processing is displayed.

In a thumbnail of the imaging procedure icon 440, no radiographic image is displayed, thereby indicating that imaging is not executed yet. In the imaging procedure (head front) relating to the imaging procedure icon 440, only the normal image processing is to be executed, whereby the imaging procedure icon 440 is not divided (duplicated) after the imaging. The radiographic image is displayed in the thumbnail of the imaging procedure icon 440.

Alternatively, the plural types of image processing can be executed on the radiographic image after the image processing unit 202 executes the normal image processing and the radiographic image having undergone the normal image processing is displayed on the display unit 124. More specifically, the radiographic image having undergone the normal image processing is displayed in the image display region 400 of the display unit 124. At this time, a thumbnail of the radiographic image having undergone the normal image processing is displayed in the imaging procedure icon 414. Then, if the plural types of image processing icon 442 indicating that the plural types of image processing are to be executed is selected via the operation unit 122, the image processing unit 202 executes the plural types of image processing such as the processing for pneumoconiosis and the black/white inversion processing. Then, the display unit 124 displays the imaging procedure icon 452 corresponding to the processing for pneumoconiosis and the imaging procedure icon 454 corresponding to the black/white inversion processing. The display unit 124 can display the radiographic image having undergone the processing for pneumoconiosis and the radiographic image having undergone the black/white inversion processing. More specifically, by a single operation of pressing the plural types of image processing icon 442, the plural types of image processing are executed on one radiographic image and resulting radiographic images are displayed.

Figure 6:
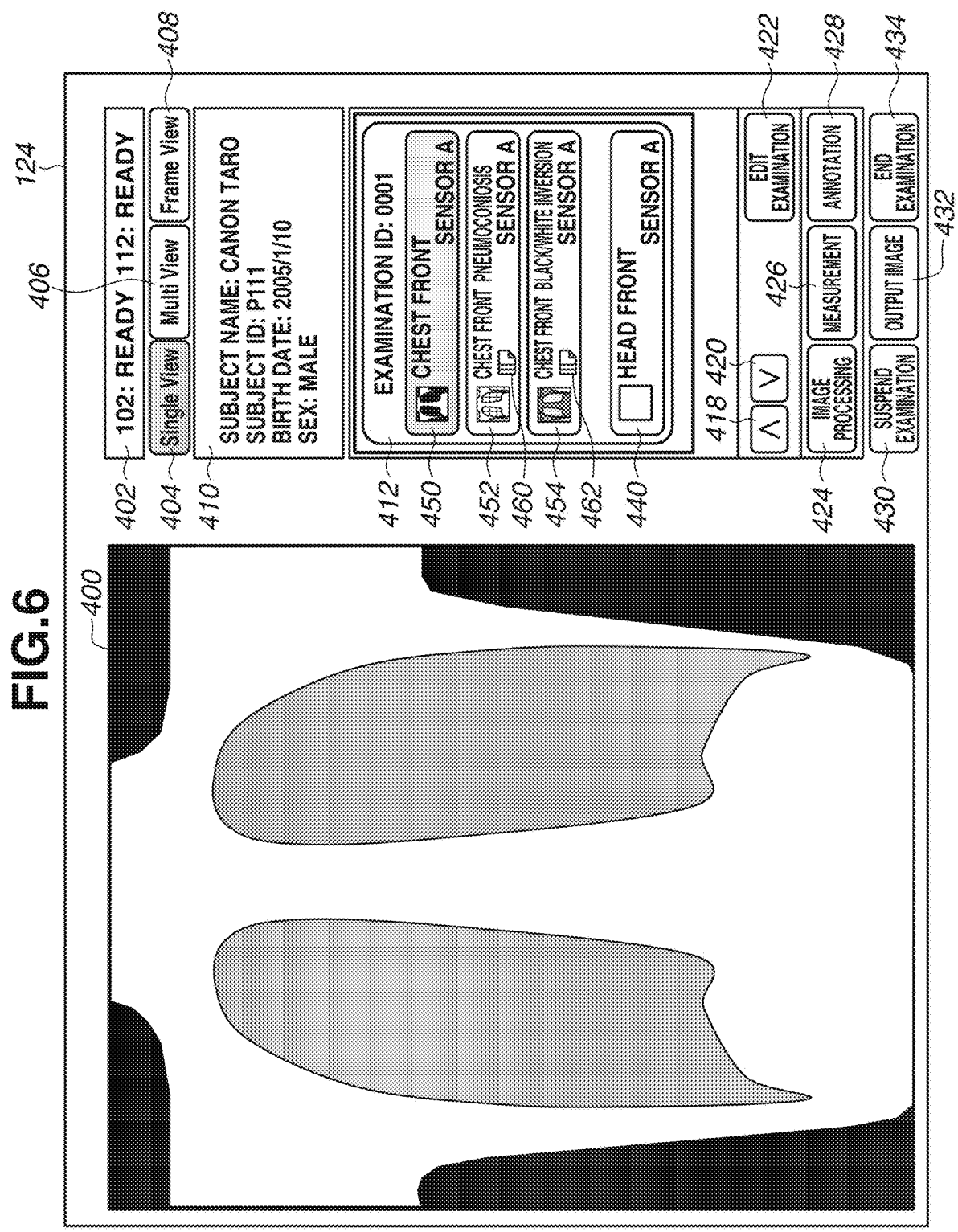
FIG. 6 illustrates an example of a display screen displayed after the radiographing system according to an exemplary embodiment executes imaging.

FIG. 6 illustrates the display screen of the display unit 124 after the imaging by the specific imaging procedure to which the plural types of image processing are set. In FIG. 5, the radiographic image corresponding to the imaging procedure icon 454, which is located at the lowermost position among the imaging procedure icons 450, 452, and 454, is displayed in the image display region 400. In this case, the radiographic image to be displayed in the image display region 400 can be changed. If the operator selects the imaging procedure icon 450 using the operation unit 122, the display unit 124 can display the radiographic image having undergone the normal image processing. If the operator selects the imaging procedure icon 452 using the operation unit 122, the display unit 124 can display the radiographic image having undergone the processing for pneumoconiosis.

In FIG. 6, the radiographic image corresponding to the imaging procedure icon 450 is displayed. A display form such as color and shape of the imaging procedure icon 450 corresponding to the radiographic image displayed in the image display region 400 is changed. Since the imaging procedure icon 450 is the icon corresponding to the normal image processing, the operator can recognize that the radiographic image (original image) having undergone the normal image processing is displayed.

Figure 7:
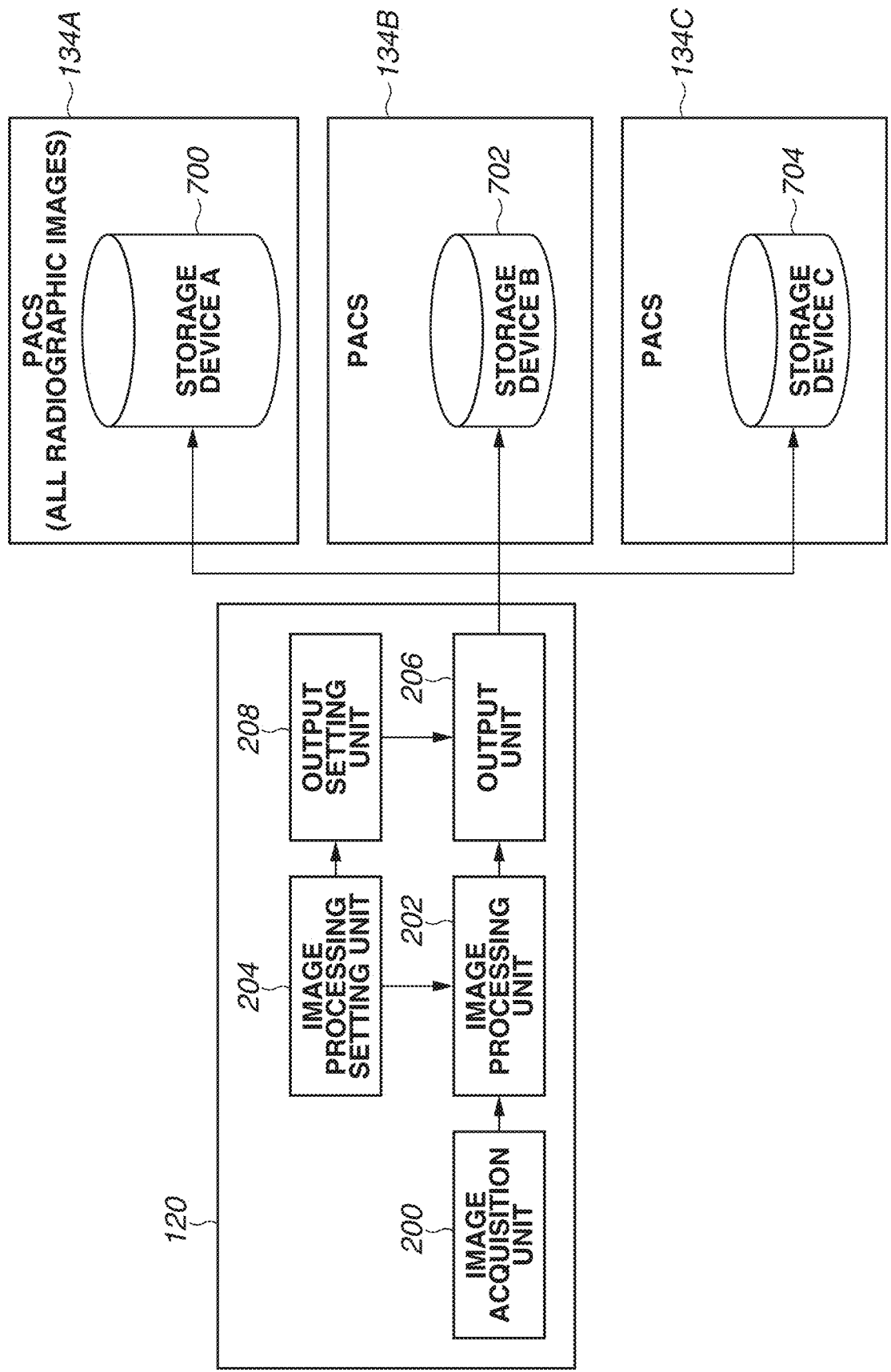
FIG. 7 illustrates an output form of the radiographing system according to an exemplary embodiment.

FIG. 7 illustrates an output form of a radiographic image in the radiographing system.

The image processing unit 202 applies the black/white inversion processing, the processing for pneumoconiosis, etc. to generate a plurality of radiographic images while retaining the radiographic image having undergone the normal image processing. Then, the image processing unit 202 transmits the radiographic image having undergone the normal image processing, the radiographic image having undergone the black/white inversion processing, and the radiographic image having undergone the processing for pneumoconiosis to the output unit 206. In the present exemplary embodiment, the image processing unit 202 transmits the plurality of radiographic images together with the image processing information such as the normal image processing, the black/white inversion processing, and the processing for pneumoconiosis to the output unit 206.

If image processing other than the normal image processing is set by the image processing setting unit 204, the image processing information about the set image processing is transmitted to the output setting unit 208. For example, if the black/white inversion processing and the processing for pneumoconiosis are set by the image processing setting unit 204, the image processing information about the black/white inversion processing and the processing for pneumoconiosis is transmitted from the image processing setting unit 204 to the output setting unit 208. More specifically, the image processing information about the image processing set (added) by the image processing setting unit 204 is transmitted to the output setting unit 208. The image processing information about the normal image processing does not have to be transmitted to the output setting unit 208 because the normal image processing is executed on every radiographic image.

The output setting unit 208 acquires the image processing information about the image processing set (added) by the image processing setting unit 204 and sets an output destination of the plurality of radiographic images to be output by the output unit 206 based on the image processing information. The output unit 206 outputs the plurality of radiographic images to the PACS (storage device) 134 (134A, 134B, 134C).

The PACS 134 stores the radiographic images output from the output unit 206. The PACS 134 stores the radiographic images having undergone the plural types of image processing executed by the age processing unit 202 separately based on the type of the image processing. The radiographic images are stored together with the image processing information.

The PACS 134A includes a storage device 700 that stores all the radiographic images (including the radiographic image having undergone the normal image processing) imaged by the radiographing system. The PACS 134B includes a storage device 702 that stores the radiographic image having undergone the black/white inversion processing. The PACS 134C includes a storage device 704 that stores the radiographic image having undergone the processing for pneumoconiosis. While a configuration in which the three PACSs 134A to 134C are included corresponding to the type of image processing is described in the present exemplary embodiment, the one PACS 134 can include the plurality of storage devices 700, 702, and 704 that stores all the radiographic images, the radiographic image having undergone the black/white inversion processing, and the radiographic image having undergone the processing for pneumoconiosis. In the present exemplary embodiment, a plurality of storage devices that store the radiographic images corresponding to the types of image processing is to be included.

The form of setting the output destinations of the plurality of radiographic images to be output from the output unit 206 by the output setting unit 208 is described below with reference to FIGS. 8A, 8B, 9A, and 9B. FIGS. 8A, 89, 9A, and 99 illustrate a setting screen of the output setting unit 208 displayed on the display unit 124. The setting screen of the output setting unit 208 is displayed on the display unit 124. Using the operation unit 122, various icons, tags, etc. are selected and executed.

If the image processing information about the image processing set by the image processing setting unit 204 is transmitted to the output setting unit 208, the display unit 124 displays the setting screen of the output setting unit 208. Then, the operator sets the output destination of the radiographic image via the operation unit 122.

FIG. 8A illustrates an image output setting screen. On a menu 800 of the image output setting screen, a name 802 relating to the imaging procedure and the image processing, and an output setting item 804 for setting whether to set an output setting to the name 802 are displayed. An OK icon 806 for executing the output setting of the output unit 206 on the name 802 relating to the imaging procedure and the image processing, and a cancel icon 808 for cancelling the output setting thereof are displayed.

In FIG. 8A, the operator inputs "CHEST FRONT PNEUMOCONIOSIS" to the name 802 relating to the imaging procedure and the image processing, and checkmarks a checkbox in the output setting item 804 via the operation unit 122. In this way, the output setting of the output unit 206 can be executed on the radiographic image having undergone the processing for pneumoconiosis at the chest front. In FIG. 8A, the output setting is set as specific processing 1. As described above, if the setting of the output setting of the output unit 206 is executed on the setting screen in FIG. 8A, the setting screen is changed to the setting screen illustrated in FIG. 8B.

FIG. 8B illustrates an image storage setting screen. On a menu 810 of the image storage setting screen, a storage name 812 for selecting a storage device and an item 814 relating to an output condition are displayed. An OK icon 816 for executing storing in the selected storage device, and a cancel icon 818 for cancelling the storing are displayed for the output condition 814.

In FIG. 8B, the operator checkmarks the checkbox of the output condition 814 via the operation unit 122. A storage device C is selected in the storage name 812. Thus, the setting of storing the radiographic image having undergone the processing for pneumoconiosis at the chest front corresponding to specific processing 1 in the storage device C is set. The output setting unit 208 transmits the setting information to the output unit 206. Thus, the output unit 206 can set an output destination of the radiographic image having undergone the processing for pneumoconiosis at the chest front.

FIG. 9A illustrates an image output setting screen similar to that in FIG. 8A. In FIG. 9A, the operator inputs "CHEST FRONT BLACK/WHITE INVERSION" to the name 802 relating to the imaging procedure and the image processing, and checkmarks a checkbox of the output setting item 804 via the operation unit 122. In this way, the output setting of the output unit 206 can be executed on the radiographic image having undergone the black/white inversion processing at the chest front. In FIG. 9A, the output setting is set as specific processing 2. As described above, if the setting of the output setting of the output unit 206 is executed on the setting screen in FIG. 9A, the setting screen is changed to the setting screen in FIG. 9B.

FIG. 9B illustrates an image storage setting screen similar to that in FIG. 8B. In FIG. 9B, the operator checkmarks the checkbox of the output condition 814 via the operation unit 122. A storage device B is selected as the storage name 812. Thus, the setting of storing the radiographic image having undergone the black/white inversion processing at the chest front corresponding to the specific processing 2 in the storage device B is set. The output setting unit 208 transmits the setting information to the output unit 206. Thus, the output unit 206 can set an output destination of the radiographic image having undergone the black/white inversion processing at the chest front.

As described above, the radiographic images having undergone the plural types of image processing are stored separately in the storage device 134, whereby the operator can efficiently search for the radiographic image having undergone specific image processing. For example, the operator can search for the radiographic image having undergone the processing for pneumoconiosis by accessing the PACS 134C (storage device 704) to search for the radiographic image having undergone the processing for pneumoconiosis.

Figure 10:
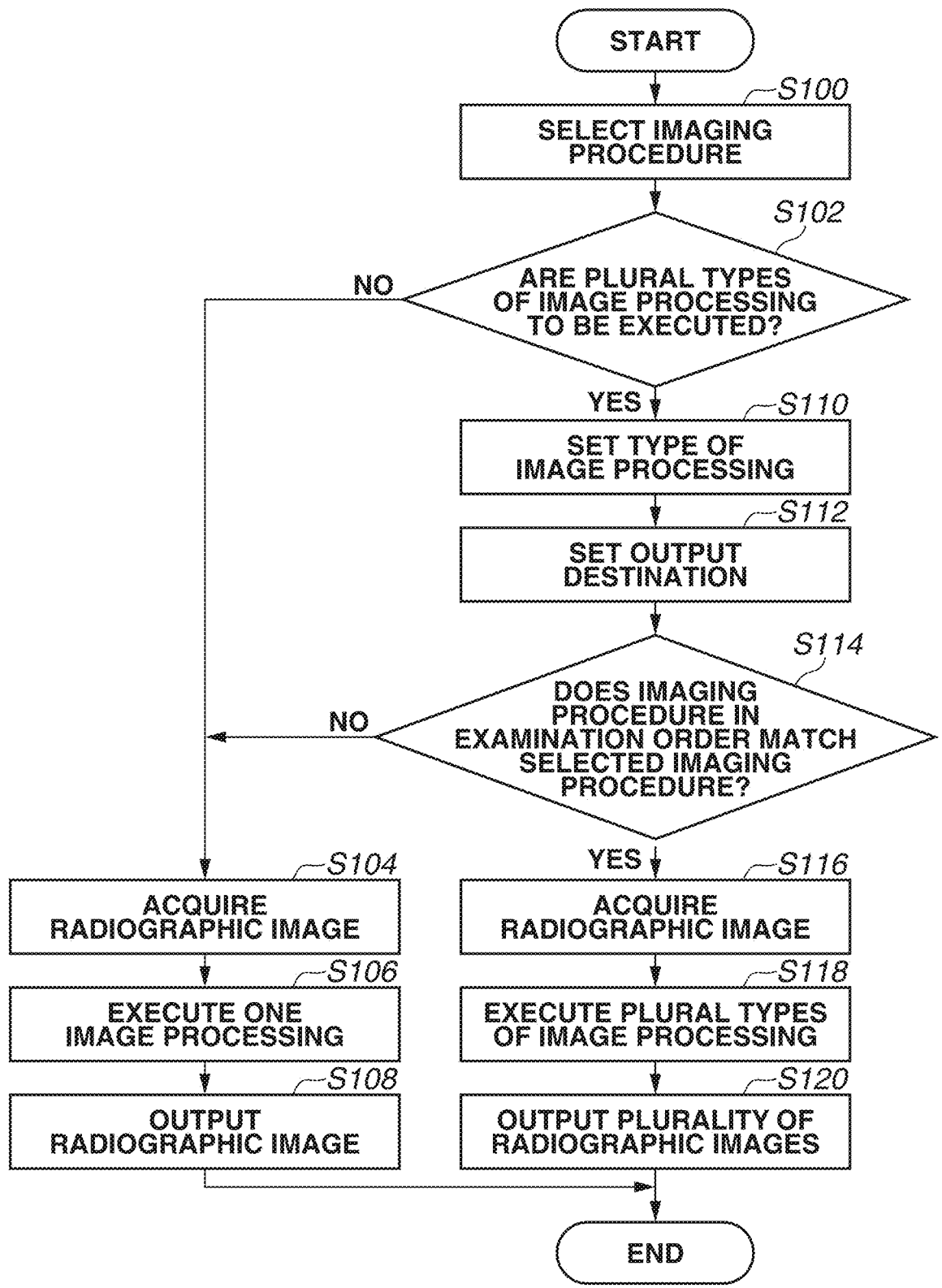
FIG. 10 is a flowchart illustrating an operation of the radiographing system according to an exemplary embodiment.

Next, operation in the radiographing system will be described below. FIG. 10 is a flowchart illustrating the operation in the radiographing system.

In step S100, a specific imaging procedure is selected before the radiographing system executes imaging. The operator selects, for example, "PROTOCOL NAME: CHEST FRONT" and "SENSOR NAME: SENSOR A" as the imaging procedure.

In step S102, whether to execute the plural types of image processing in the selected specific imaging procedure is selected. The operator selects whether to execute, for example, the black/white inversion processing and the processing for pneumoconiosis in addition to the normal image processing in the selected imaging procedure. If the plural types of image processing are not to be executed (NO in step S102), the processing proceeds to step S104. If the plural types of image processing are to be executed (YES in step S102), the processing proceeds to step S110.

In step S104, the radiographing system executes imaging based on a subject examination order transmitted from the RIS 132. In the present exemplary embodiment, the radiation detection apparatus 102 and 112 image radiation emitted from the radiation generation units 100 and 110 and output a radiographic image to the image acquisition unit 200 of the control unit 120. The image acquisition unit 200 acquires the radiographic image (image data) output from the radiation detection apparatus 102 or 112.

In step S106, the image processing unit 202 executes the normal image processing (gradation conversion to convert a pixel value into a density (luminance), etc.) on the radiographic image output from the image acquisition unit 200. In the present exemplary embodiment, one image processing is executed on one radiographic image to generate one radiographic image.

In step S108, the output unit 206 outputs the radiographic image having undergone the normal image processing (one image processing) to the PACS (storage device) 134. At this time, the operation of the radiographing system in the case of executing the normal image processing (one image processing) ends.

In step S110, the operator sets the plural types of image processing to the selected imaging procedure using the image processing setting unit 204. The operator sets the setting of executing, for example, the black/white inversion processing and the processing for pneumoconiosis in addition to the normal image processing to the selected imaging procedure.

In step S112, the operator sets an output destination of the plurality of radiographic images to be output from the output unit 206 using the output setting unit 208. The output setting unit 208 can set an output setting in which the plurality of radiographic images is separately output. The output setting unit 208 enables the plurality of radiographic images to be output separately according to the type of image processing. The output setting unit 208 can set, for example, an output setting in which the radiographic image having undergone the black/white inversion processing and the radiographic image having undergone the processing for pneumoconiosis are output to the PACSs (storage devices) 134B and 134C, respectively.

As described above, in steps S110 and S112, the type of image processing and the output of the plurality of radiographic images in the case of executing the plural types of image processing are set to the selected imaging procedure. This is a pre-setting prior to the imaging.

In step S114, the control unit 120 receives the subject examination order from the RIS 132. The control unit 120 determines whether the imaging procedure included in the subject examination order received from the RIS 132 (external apparatus) matches the imaging procedure to which the plural types of image processing are set. At this time, the control unit 120 functions as a determination unit. The imaging procedure to which the plural types of image processing are set is the imaging procedure selected before the imaging. If the imaging procedures do not match (NO in step S114), the processing proceeds to step S104. If the imaging procedures match (YES in step S114), the processing proceeds to step S116.

In step S116, the radiographing system executes imaging based on the subject examination order transmitted from the RIS 132. In the present exemplary embodiment, the radiation detection apparatuses 102 and 112 image radiation emitted from the radiation generation units 100 and 110, respectively, and output a radiographic image to the image acquisition unit 200 of the control unit 120. The image acquisition unit 200 acquires the radiographic image (image data) output from the radiation detection apparatuses 102 and 112.

In step S118, the image processing unit 202 executes the plural types of image processing on the radiographic image based on the image processing information set by the image processing setting unit 204. The image processing unit 202 executes, for example, the normal image processing, the black/white inversion processing, and the processing for pneumoconiosis on one radiographic image. In the present exemplary embodiment, two or more types of image processing are executed on one radiographic image to generate two or more radiographic images.

In step S120, the output unit 206 outputs the plurality of radiographic images to the PACSs (storage devices) 134A to 134C set as the output destinations by the output setting unit 208. At this time, the operation of the radiographing system in the case of executing the plural types of image processing ends.

The radiographing system (control apparatus) according to the exemplary embodiment includes the image acquisition unit 200 that acquires a radiographic image based on radiation transmitted through a subject, the image processing setting unit 204 that sets plural types of image processing to a specific imaging procedure, the image processing unit 202 that executes the plural types of image processing set by the image processing setting unit 204 on a radiographic image acquired by the specific imaging procedure to generate a plurality of radiographic images, and the output unit 206 that outputs, to the storage device 134, the plurality of radiographic images generated by the image processing unit 202 separately based on the type of image processing. Accordingly, the plurality of radiographic images having undergone the plural types of image processing can be efficiently generated, and the plurality of radiographic images can be separately stored.

The radiographing system (control apparatus) according to the exemplary embodiment can also include the control unit 120 (determination unit) that determines whether an imaging procedure included in a subject examination order matches the specific imaging procedure, and the image processing unit 202 that, in a case where the imaging procedure included in the subject examination order matches the specific imaging procedure, executes the plural types of image processing set by the image processing setting unit 204 on the radiographic image acquired by the specific imaging procedure to generate the plurality of radiographic images. Accordingly, the plurality of radiographic images having undergone the plural types of image processing can be efficiently generated.

The present disclosure can also be achieved by processing in which a program for achieving one or more functions (especially plural types of image processing and image output) is supplied to a control apparatus via a network or a storage medium and one or more processors of a computer in the control apparatus reads and executes the program. The present disclosure can also be achieved by a circuit (e.g., application-specific integrated circuit (ASIC)) that achieves one or more functions.

Embodiments can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-224974, filed Nov. 22, 2017, which is hereby incorporated by reference herein in its entirety.

What is claimed is:

1. A radiographing system comprising:
    an image acquisition unit configured to acquire a radiographic image based on radiation transmitted through a subject;
    an image processing setting unit configured to set plural types of image processing to a specific imaging procedure;
    an image processing unit configured to execute the set plural types of image processing on an acquired radiographic image to generate a plurality of radiographic images; and
    an output unit configured to separately output the generated plurality of radiographic images based on a type of the image processing.

2. The radiographing system according to claim 1, wherein the image processing unit executes first image processing and second image processing on one radiographic image to generate the plurality of radiographic images.

3. The radiographing system according to claim 1, wherein the image processing setting unit sets the type of image processing for each imaging procedure.

4. The radiographing system according to claim 1, further comprising a display control unit configured to display the generated plurality of radiographic images on a display unit,
    wherein the display control unit causes the display unit to display information about the set plural types of image processing in an imaging procedure icon corresponding to the specific imaging procedure.

5. The radiographing system according to claim 4, wherein the display control unit causes the display unit to display one or more of an image processing icon indicating that the set plural types of image processing are to be executed or text information indicating that the set plural types of image processing are to be executed.

6. The radiographing system according to claim 5, further comprising an operation unit configured to select the image processing icon,
    wherein if the image processing icon is selected, the image processing unit executes the set plural types of image processing on the radiographic image to generate the plurality of radiographic images.

7. The radiographing system according to claim 4, wherein a duplication mark indicating that the set plural types of image processing are applied to the radiographic image and the radiographic image is duplicated is displayed in the imaging procedure icon.

8. The radiographing system according to claim 4, wherein the imaging procedure icon is displayed such that a case in which the set plural types of image processing are to be executed and a case in which the set plural types of image processing are not to be executed can be distinguished.

9. The radiographing system according to claim 1, wherein the image processing unit executes one or more of black/white inversion processing or processing for pneumoconiosis on the radiographic image to generate the plurality of radiographic images.

10. The radiographing system according to claim 1, further comprising an output setting unit configured to set an output of the output unit,
    wherein when the plural types of image processing are set by the image processing setting unit, image processing information about the set plural types of image processing is transmitted to the output setting unit, and the output setting unit sets the output of the output unit based on the set plural types of image processing.

11. The radiographing system according to claim 1, further comprising a determination unit configured to determine whether an imaging procedure included in a subject examination order matches the specific imaging procedure to which the plural types of image processing is set,
    wherein in a case where the imaging procedure included in the subject examination order matches the specific imaging procedure, the image processing unit executes the set plural types of image processing on the radiographic image to generate the plurality of radiographic images.

12. A radiographing system comprising:
    an image acquisition unit configured to acquire a radiographic image based on radiation transmitted through a subject;
    an image processing setting unit configured to set plural types of image processing to a specific imaging procedure;
    a determination unit configured to determine whether an imaging procedure included in a subject examination order matches the specific imaging procedure; and
    an image processing unit configured to execute the set plural types of image processing on the acquired radiographic image to generate a plurality of radiographic images in a case where the imaging procedure included in the subject examination order matches the specific imaging procedure.

13. A radiographing method comprising:
    acquiring a radiographic image based on radiation transmitted through a subject;
    setting plural types of image processing to a specific imaging procedure;
    executing the set plural types of image processing on the acquired radiographic image to generate a plurality of radiographic images; and
    separately outputting the plurality of generated radiographic images based on a type of the image processing.

14. A radiographing method comprising:
    acquiring a radiographic image based on radiation transmitted through a subject;
    setting plural types of image processing to a specific imaging procedure;
    determining whether an imaging procedure included in a subject examination order matches the specific imaging procedure; and
    executing the set plural types of image processing on the acquired radiographic image to generate a plurality of radiographic images in a case where the imaging procedure included in the subject examination order matches the specific imaging procedure.

15. A control apparatus comprising:
    an image acquisition unit configured to acquire a radiographic image based on radiation transmitted through a subject;
    an image processing setting unit configured to set plural types of image processing to a specific imaging procedure;
    an image processing unit configured to execute the plural types of image processing set by the image processing setting unit on a radiographic image acquired by the specific imaging procedure to generate a plurality of radiographic images; and an output unit configured to output, to a storage device, the plurality of radiographic images generated by the image processing unit separately according to a type of the image processing.

16. A control apparatus comprising:

an image acquisition unit configured to acquire a radiographic image based on radiation transmitted through a subject;

an image processing setting unit configured to set plural types of image processing to a specific imaging procedure;

a determination unit configured to determine whether an imaging procedure included in an examination order received from an external apparatus matches the specific imaging procedure; and an image processing unit configured to execute the plural types of image processing set by the image processing setting unit on a radiographic image acquired by the specific imaging procedure to generate a plurality of radiographic images in a case where the imaging procedure included in the examination order received from the external apparatus matches the specific imaging procedure.

17. A non-transitory computer-readable storage medium that stores a program for causing a computer to execute a method, the method comprising:

acquiring a radiographic image based on radiation transmitted through a subject;

setting plural types of image processing to a specific imaging procedure;

executing the set plural types of image processing on the acquired radiographic image to generate a plurality of radiographic images; and separately outputting the plurality of generated radiographic images based on a type of the image processing.

18. A non-transitory computer-readable storage medium that stores a program for causing a computer to execute a method, the method comprising:

acquiring a radiographic image based on radiation transmitted through a subject;

setting plural types of image processing to a specific imaging procedure;

determining whether an imaging procedure included in a subject examination order matches the specific imaging procedure; and executing the set plural types of image processing on the acquired radiographic image to generate a plurality of radiographic images in a case where the imaging procedure included in the subject examination order matches the specific imaging procedure.

* * * * *